United States Patent [19]

Yoshino et al.

[11] Patent Number: 5,274,185
[45] Date of Patent: Dec. 28, 1993

[54] METHOD OF PRODUCING NAPHTHALENE DICARBOXYLIC ACID

[75] Inventors: Tadahiro Yoshino; Tadao Wakui, both of Chiba, Japan

[73] Assignee: Kawasaki Steel Corporation, Japan

[21] Appl. No.: 912,824

[22] Filed: Jul. 13, 1992

Related U.S. Application Data

[63] Continuation-in-part of Ser. No. 649,425, Feb. 1, 1991, abandoned.

[51] Int. Cl.$^5$ .............................................. C07C 51/09
[52] U.S. Cl. .................................. 562/483; 562/485; 562/486; 562/487; 562/488
[58] Field of Search ............... 562/483, 485, 486, 487, 562/488

[56] References Cited

U.S. PATENT DOCUMENTS 3,650,907  3/1972  McNelis et al. ...................... 203/96
4,794,195  12/1988  Hayashi et al. ...................... 562/414

OTHER PUBLICATIONS

Chemical Abstracts, vol. 102, No. 21, Entry 185547z, (1985).

*Primary Examiner*—José G. Dees
*Assistant Examiner*—Vera C. Clarke
*Attorney, Agent, or Firm*—Bierman and Muserlian

[57] ABSTRACT

A high purity naphthalene dicarboxylic acid (NDCA) is easily and rapidly produced by reacting a dialkylester of NDCA within a temperature range of 70°–350° C. in a solvent including at least one mono-carboxylic acid of R—COOH (wherein R has a total carbon number of not more than 9 and is a hydrogen atom, an alkyl group, a cycloalkyl group, a phenyl group, a moiety formed by bonding at least one group selected from an alkyl group, a cycloalkyl group, a phenyl group, an alkylene group, a cycloalkylene group and a phenylene group to a carbonyl group or an ether group, or a moiety formed by substituting a part or whole of hydrogen atoms in one group or a moiety selected from an alkyl group, a cycloalkyl group, a phenyl group and the above moiety with at least one group selected from an alkyl group, a cycloalkyl group and a phenyl group other than the above selected group, and a part or whole of hydrogen atoms in R may be substituted with halogen atom, provided that the total carbon number of R does not include a carbon number of carbonyl group) in the presence of an esterification catalyst and then subjecting the reaction product to a solid-liquid separation.

11 Claims, No Drawings

METHOD OF PRODUCING NAPHTHALENE DICARBOXYLIC ACID

This application is a continuation-in-part of the co-pending application Ser. No. 649,425 filed Feb. 1, 1991, now abandoned.

BACKGROUND OF THE INVENTION

1. Field of the Invention

This invention relates to a method of producing a high purity naphthalene dicarboxylic acid.

2. Related Art Statement

Naphthalene dicarboxylic acid (hereinafter abbreviated as NDCA), particularly 2,6-naphthalene dicarboxylic acid (2,6-NDCA) is noticed as a starting material for dye and medicine and a starting material for polyethylene naphthalate resin (PEN) and liquid crystal polyester resin (LCP). In case of PEN using dimethyl 2,6-naphthalene dicarboxylate (2,6-NDCA dimethyl) as a starting material, since 2,6-NDCA dimethyl is easy in the purification and available in a high purity, the production has already been put into practical use. However, in case of LCP using 2,6-NDCA as a starting material, excellent properties are attained, but it is difficult to obtain a high purity 2,6-NDCA, so that the production is not yet put into practical use.

The reason why the production of high purity 2,6-NDCA is difficult is due to the fact that the purification is very difficult as mentioned in the features 1)-3):

1) There is substantially no solvent sufficiently dissolving 2,6-NDCA, so that the recrystallization is impossible.

2) The vapor pressure of 2,6-NDCA is very low, so that the purification through distillation or sublimation is impossible.

3) Since 2,6-NDCA does not melt (which has no melting point and decomposes by heating), the crystallization is impossible.

Up to the present, many methods of purifying 2,6-NDCA have been proposed, but they are not for direct purification. For example, there have been known a method wherein 2,6-NDCA is converted into an acid chloride and then purified (Japanese Patent laid open No. 62-169747), a method wherein 2,6-NDCA is converted into an alkali salt and then purified (Japanese Patent Application Publications No. 45-7738, No. 45-13096, No. 52-20993, No. 52-20994, No. 56-3858 and No. 57-36901), a method wherein 2,6-NDCA is converted into an amine salt and then purified (Japanese Patent Application Publications No. 56-48498 and No. 57-14331), a method wherein 2,6-NDCA is converted into an ammonium salt and then purified (Japanese Patent laid open No. 51-52163) and the like.

In the method of purifying 2,6-NDCA after the conversion into acid chloride, however, it is required to use an expensive halogenating agent such as thionyl chloride. Furthermore, this method can not be said to be an industrially suitable one considering the treatment for chloride by-produced in the turning of acid chloride to carboxylic acid and the material of the equipment durable to corrosion. On the other hand, in the methods of purifying after the conversion into various salts, it is difficult to remove position isomers and monocarboxylic acid included as impurities in 2,6-NDCA, and a high purity usable as a starting material for LCP can not be obtained.

A simple method of producing a high purity 2,6-NDCA usable as a starting material for LCP is the production from 2,6-NDCA dialkylester. Since 2,6-NDCA dialkylester, for example, 2,6-NDCA dimethyl can be purified by distillation or recrystallization, crude 2,6-NDCA is converted into dialkylester with an alcohol or the like and purified to obtain a high purity 2,6-NDCA dialkylester, from which a high purity 2,6-NDCA can be obtained.

However, when 2,6-NDCA dialkylester is converted into 2,6-NDCA through hydrolysis with a strong alkali, if the strong alkali is sodium hydroxide, the resulting 2,6-NDCA disodium salt is hardly soluble in water, so that the reaction solution changes to a gel as the hydrolysis reaction proceeds and finally renders into a solid soap to stop the reaction. Even when using potassium hydroxide as a strong alkali, as the reaction proceeds, the reaction solution changes to a slurry having a high viscosity, so that the reaction should be carried out with a fairly diluted solution for preventing such a change. Furthermore, the resulting 2,6-NDCA consumes the alkali to produce a salt, so that it is necessary to use an alkali in an amount of not less than equivalent of resulting carboxyl group. Moreover, the particle size of 2,6-NDCA in the slurry produced when the resulting 2,6-NDCA dialkali salt is neutralized with an acid is very small, so that the slurry has a high viscosity and a high water content. As a result, the treatment for solid-liquid separation is charged with difficulties and also the washing becomes difficult, so that there are caused problems that the alkali metal salt by-produced in the neutralization incorporates into final 2,6-NDCA and a great energy is taken for the drying after the washing.

On the other hand, the use of the acid catalyst can substantially avoid the aforementioned drawbacks caused in the hydrolysis with the alkali catalyst, but the reaction is very slow and can not put into practical use. For instance, even when 2,6-NDCA is boiled in an aqueous solution of strong acid, hydrolysis reaction does not proceed at all.

SUMMARY OF THE INVENTION

It is, therefore, an object of the invention to solve the above problems of the conventional technique and to provide a method of easily and rapidly producing a high purity NDCA from NDCA dialkylester.

The inventors have made various studies on a method of producing NDCA from NDCA dialkylester without an alkali catalyst and found that when a monocarboxylic acid containing no unsaturated bond (indicating ethylenically double bond and acetylnically triple bond) is used as a solvent, an ester exchange reaction is easily caused by heating in the presence of an esterification catalyst to produce NDCA. Furthermore, it has been found that the resulting NDCA is insoluble in the above monocarboxylic acid solvent and has a large particle size, so that the solid-liquid separation can easily be carried out and the high purity NDCA is obtained only by washing.

The invention is based on the above knowledge, and lies in a method of producing naphthalene dicarboxylic acids, which comprises reacting a dialkylester of naphthalene dicarboxylic acid within a temperature range of 70°-350° C. in a solvent including at least one monocarboxylic acid represented by the following formula:

(wherein R has a total carbon number of not more than 9 and is a hydrogen atom, an alkyl group, a cycloalkyl group, a phenyl group, a moiety formed by bonding at least one group selected from an alkyl group, a cycloalkyl group, a phenyl group, an alkylene group, a cycloalkylene group and a phenylene group to a carbonyl group or an ether group, or a moiety formed by substituting a part or whole of hydrogen atoms in one group or moiety selected from an alkyl group, a cycloalkyl group, a phenyl group and the above moiety with at least one group selected from an alkyl group, a cycloalkyl group and a phenyl group other than the above selected group, and a part or whole of hydrogen atoms in R may be substituted with halogen atom, provided that the total carbon number of R does not include a carbon number of carbonyl group) in the presence of an esterification catalyst and then subjecting the resulting reaction product to a solid-liquid separation to obtain a high purity naphthalene dicarboxylic acid.

DESCRIPTION OF THE PREFERRED EMBODIMENTS

The invention will concretely be described below.

According to the invention, NDCA dialkylester used as a starting material is made from NDCA (and its derivative) and aliphatic alcohol (and its derivative). As the NDCA dialkylester, there are 10 kinds of position isomers, but anyone of these isomers may be used. As to alkyl group of the NDCA dialkylester, the carbon number and branched degree are not particularly critical. The alkyl group preferably includes methyl group, ethyl group, propyl group, isopropyl group, butyl group, isobutyl group, hexyl group and octyl group, among which methyl group is favorable. As the NDCA dialkylester, mention may be made of dimethyl ester, diethyl ester, dipropyl ester and dioctyl ester of 1,2-, 1,3-, 1,4-, 1,5-, 1,6-, 1,7-, 1,8-, 2,3-, 2,6- and 2,7-naphthalene dicarboxylic acids and so on. Among these esters, 1,5-NDCA dimethyl, 2,6-NDCA dimethyl and 2,7-NDCA dimethyl are preferable from a viewpoint of easiness in the conversion of NDCA to dialkylester and the value of resulting NDCA as an industrial material, and particularly 2,6-NDCA dimethyl is favorable.

The esterification catalyst used in the invention is a catalyst usually used for the esterification reaction of carboxylic acid with alcohol or phenol, which preferably includes a strong acid, a metal salt and a metal oxide.

As the strong acid, mention may be made of sulfuric acid, nitric acid, hydrochloric acid, toluene sulfonic acid, fluoroacetic acid, boron trifluoride, strong acid-type ion exchange resin, Nafion (trade name, made by E. I. Dupont) and the like, among which sulfuric acid is most preferable. As the metal salt and metal oxide, mention may be made of oxides, sulfates, chlorides, sulfides, bromides, acetates and the like of a metal selected from the group consisting of zinc, lead, copper, manganese, cobalt, iron, nickel, antimony, cadmium, tin, mercury, aluminum, bismuth, selenium and tellurium.

Among these esterification catalysts, the strong acid is suitable, since it can prevent metal ions from contaminating the resulting NDCA as impurities. The most preferable strong acid is sulfuric acid because it is nonvolatile and easily available.

As the amount of the catalyst becomes larger, the reaction becomes fast and NDCA is obtained in a high yield for a short time. While, the treatment of waste liquid and the purification for removing the catalyst from the resulting NDCA come into problems. It is necessary to select the optimal amount of the strong acid. For example, when the strong acid is used as an esterification catalyst, the amount of the strong acid is 0.01–1.0 mol/kg, particularly 0.1–0.6 mol/kg as a concentration of hydrogen ion per 1 kg of the monocarboxylic acid solvent.

The monocarboxylic acid used as a solvent in the invention is represented by the general formula of R—COOH (wherein R has a total carbon number of not more than 9 and is a hydrogen atom, an alkyl group, a cycloalkyl group, a phenyl group, a moiety formed by bonding at least one group selected from an alkyl group, a cycloalkyl group, a phenyl group, an alkylene group, a cycloalkylene group and a phenylene group to a carbonyl group or an ether group, or a moiety formed by substituting a part or whole of hydrogen atoms in one group selected from an alkyl group, a cycloalkyl group, a phenyl group and the above moiety with at least one group selected from an alkyl group, a cycloalkyl group and a phenyl group other than the above selected group, and a part or whole of hydrogen atoms in R may be substituted with halogen atom, provided that the total carbon number of R does not include a carbon number of carbonyl group).

The monocarboxylic acid in which R is hydrogen atom is formic acid. As the monocarboxylic acid in which R is the alkyl group, mention may be made of acetic acid, propionic acid, butyric acid, valeric acid, caproic acid, enanthic acid, caprylic acid, pelargonic acid, capric acid and so on. As the monocarboxylic acid in which R is the cycloalkyl group, mention may be made of cyclopropane carboxylic acid, cyclobutane carboxylic acid, cyclopentane carboxylic acid, cyclohexane carboxylic acid, cycloheptane carboxylic acid and so on. As the monocarboxylic acid in which R is the phenyl group, mention may be made of benzoic acid, and so on. Furthermore, as the monocarboxylic acid in which R is the group or moiety other than an alkyl group, a cycloalkyl group and a phenyl group, ketonic acid such as pyruvic acid or the like, parachloro benzoic acid, p-methoxybenzoic acid, 4-acetylbenzoic acid, trifluoro acetic acid and phenyl acetic acid may be used. The monocarboxylic acid used in the invention is not limited to the aforementioned acids. Moreover, formic acid, acetic acid, propionic acid and benzoic acid are preferable as the monocarboxylic acid, among which acetic acid is most preferable. According to the invention, the aforementioned monocarboxylic acids may be used alone or in admixture.

On the contrary, when unsaturated carboxylic acids, polyvalent carboxylic acids, aliphatic monocarboxylic acids having a carbon number of 11 or more and alicyclic monocarboxylic acids having a carbon number of 11 or more are used as a solvent, these acids themselves react by heating in the presence of the strong acid and hence the resulting reaction product is incorporated into NDCA as an impurity. For instance, in case of the unsaturated carboxylic acid, the reaction of the unsaturated bond is caused to bring about gelation of the solvent and coloration of the product. In case of the polyvalent carboxylic acid and aliphatic and alicyclic monocarboxylic acids having a carbon number of 11 or more, black and insoluble product is formed. In any case, when using the carboxylic acid having a carbon number of 11 or more as a solvent irrespective of saturated, unsaturated, aromatic, aliphatic and alicyclic, the reaction rate lowers and the viscosity fairly rises and the solid-liquid separation becomes difficult. Therefore, the use of these acids as a solvent can not achieve the object of the invention. The high purity NDCA can not be obtained only by a simple washing as a purification treatment after the solid-liquid separation of the reaction product.

In the reaction system according to the invention, an alkylester of monocarboxylic acid is produced by ester exchange reaction (acidloysis) between NDCA dialkylester and the monocarboxylic acid solvent. Since this reaction easily reaches to equilibrium condition, it is favorable to remove the resulting alkylester of monocarboxylic acid from the reaction system in order to obtain the high purity NDCA after the completion of the reaction.

As a typical means for removing the alkylester of monocarboxylic acid, there are a procedure of escaping out the alkylester of monocarboxylic acid from the reaction system and a procedure of adding water to the reaction system to hydrolyze the resulting alkylester of monocarboxylic acid into monocarboxylic acid and alcohol. According to these procedures, the equilibrium state of the ester exchange reaction is shifted toward a side of producing objective product to complete the reaction.

As the former procedure, there are a method of conducting the reaction in an open system, a method of blowing an inert gas into the open reaction system to promote the removal of the above alkylester, a method of conducting the reaction under pressure to escape gaseous alkylester of monocarboxylic acid through a leak valve, a method of condensing and collecting the alkylester of monocarboxylic acid in a condenser equipment irrespective of pressureless or pressurization, and the like, which may properly be selected in accordance with the properties of monocarboxylic acid used.

In the latter procedure, an amount of water required for the completion of the equilibrium reaction is added to the solvent. That is, the amount of water is not less than 2 times of mol equivalent of NDCA dialkylester used as a starting material, preferably not more than 50% by weight. When the amount of water in the solvent exceeds 50% by weight, the reaction becomes undesirably slower. The preferable water amount is not more than 20% by weight and not less than 2 times of mol equivalent of NDCA dialkylester.

The amount of the monocarboxylic acid solvent containing not more than 50% by weight of water is not particularly restricted. However, if the amount of the solvent is too large to NDCA dialkylester, the yield of NDCA per one batch decreases, which comes into problem in the production efficiency, while when it is too small, the reaction solution changes to a high viscosity slurry. Therefore, the preferable amount of the monocarboxylic acid solvent is within a range of 100–1000 parts by weight based on 100 parts by weight of NDCA dialkylester.

Moreover, an inert solvent giving no influence on the reaction may be included in the monocarboxylic acid solvent used in the invention. As such a solvent, there are typically mentioned hydrocarbons such as toluene, xylene, biphenyl, alkylnaphthalene, mineral oil and the like; methyl ethyl ketone, diphenyl ether and silicone oil.

According to the invention, the reaction temperature is required to be within a range of 70°–350° C. When the reaction temperature is lower than 70° C., the reaction hardly proceeds, while when it exceeds 350° C., decarbonation and decomposition reaction of the resulting NDCA undesirably occurs. The preferable reaction temperature is within a range of 120°–300° C.

The pressure in the reaction system is not particularly restricted, but it is desirable that when using a low boiling point carboxylic acid such as formic acid or acetic acid, the reaction system is held at a higher reaction temperature under an elevated pressure. In the latter case, the reaction temperature under is preferably within a range of 120°–200° C. For instance, in case of acetic acid, when the reaction temperature exceeds 200° C., the vapor pressure reaches to about 10 kg/cm$^2$, so that the pressure resistance of the reaction vessel comes into problem.

Moreover, the optimum combination of conditions in the production method according to the invention is that 2,6-NDCA dimethyl is reacted at 120°–200° C. in an aqueous solution of 80–95% by weight of acetic acid as a solvent in the presence of sulfuric acid as a catalyst, or that 2,6-NDCA dimethyl is reacted at 120°–200° C. in glacial acetic acid as a solvent in the presence of sulfuric acid as a catalyst while removing out the resulting methyl acetate from the reaction system.

In order to fully utilize the easiness of solid-liquid separation between the resulting NDCA and carboxylic acid solvent and the simplicity of purification as a feature of the invention at maximum, it is preferable that the reaction is completed so as not to leave 2,6-NDCA dialkylester. Even if the completion of the reaction is insufficient, no solvent dissolving the resulting NDCA is substantially existent, so that the high purity NDCA can simply be obtained by adding only an operation of washing unreacted NDCA dialkylester with a solvent.

As a typical example of the solid-liquid separation, use may be made of filtration by suction, filtration under pressure, centrifugal filtration, filtration under vacuum, gravity filtration, supernatant filtration, squeezing filtration and the like, which can favorably be used.

The following examples are given in illustration of the invention and are not intended as limitations thereof.

At first, analysis adopted in the following examples will be described below.

1) Quantitative determination of NDCA

The quantitative determination of NDCA (product), NDCA monoalkylester (intermediate) and NDCA dialkylester (starting material) in the reaction product was made by HPLC analysis [column: Inertsil ODS (made by Gasukuro Kogyo Inc.) 4.2×250 mm, column temperature: 40° C., flow rate: 0.85 ml/min, detector: 260 nm UV, mobile phase: mixture of $CH_3CN$/THF/$KH_2PO_4$/$H_3PO_4$/tetrabutyl ammonium bromide/water, sample: 5 μl], from which NDCA purity was determined. Moreover, substances other than the above three compounds were not detected in all examples and comparative examples.

2) Measurement of whiteness degree

The whiteness degree was measured by a color analysis system of U3210 model (made by Hitachi, Ltd.) under the criterion that a white standard plate of aluminum oxide was 100.

EXAMPLE 1

Into a glass autoclave of 1 liter capacity were charged 200 g of 2,6-NDCA dimethyl, 370 g of galcial acetic acid, 30 g of water and 6.0 g of concentrated sulfuric acid, and then temperature was raised at 5° C./min with stirring. As the reaction temperature was raised, 2,6-NDCA dimethyl was gradually dissolved and finally rendered into a uniform transparent solution at 130° C. Then, white precipitates began to produce at about 160° C.

When the temperature reached to 170° C., the reaction was continued at this temperature for 8 hours. Thereafter, the reaction product was cooled and filtered by suction to separate the solvent therefrom. The separated solid product was subjected to HPLC analysis as it was, whereby the purity of NDCA was measured. An amount corresponding to only 0.004% by weight of the resulting solid product was contained in the solvent removed by the filtration. After the solid product was ashen in a muffle furnace, a content of alkali metal ion was confirmed by a spectral analysis to be zero.

The solid product was washed with 400 ml of hot ethanol three times to sufficiently remove the solvent and acid and then dried under vacuum to obtain a powdery product. Next, the whiteness degree of the thus obtained powder was measured to obtain a result as shown in Table 1.

EXAMPLES 2-8

The same procedure as in Example 1 was repeated except that formic acid, propionic acid, valeric acid, caproic acid, caprylic acid, capric acid or benzoic acid was used instead of glacial acetic acid as a solvent. Only in case of using capric acid, the reaction solution was colored into yellow, but in case of the other solvents, the reaction solution was not colored likewise Example 1.

In case of using benzoic acid, the reaction system was solidified in the cooling after the completion of the reaction, so that it was homogeneously pulverized and then subjected to HPLC analysis. The measurement of the whiteness degree was carried out by reheating the powder, subjecting to solid-liquid separation through hot filtration and removing the solvent through washing with hot ethanol. The measured results are also shown in Table 1.

COMPARATIVE EXAMPLES 1-3

The same procedure as in Example 1 was repeated except that lauric acid, palmitic acid or adipic acid was used instead of glacial acetic acid as a solvent. The color of the reaction solution changed to brown in case of lauric acid and black in case of palmitic acid and adipic acid.

In any case, the reaction system was solidified in the cooling after the completion of the reaction, so that the HPLC analysis and measurement of whiteness degree were made in the same manner as in Example 8. The results are also shown in Table 1.

TABLE 1

|  | Carboxylic acid solvent (carbon number) | Purity of 2,6-NDCA (%) | Whiteness degree of 2,6-NDCA |
|---|---|---|---|
| Example 2 | formic acid (C1) | 99 | 93.4 |
| Example 1 | acetic acid (C2) | 99 | 93.6 |
| Example 3 | propionic acid (C3) | 99 | 93.2 |
| Example 4 | valeric acid (C5) | 92 | 92.5 |
| Example 5 | caproic acid (C6) | 86 | 92.8 |
| Example 6 | caprylic acid (C8) | 82 | 90.3 |
| Example 7 | capric acid (C10) | 71 | 90.2 |
| Example 8 | benzoic acid (C7) | 78 | 93.5 |
| Comparative Example 1 | lauric acid (C12) | 65 | 73.0 |
| Comparative Example 2 | palmitic acid (C16) | 58 | 28.0 |

TABLE 1-continued

|  | Carboxylic acid solvent (carbon number) | Purity of 2,6-NDCA (%) | Whiteness degree of 2,6-NDCA |
|---|---|---|---|
| Comparative Example 3 | adipic acid (C6) | 55 | 15.0 |

EXAMPLE 9

Into an autoclave of 1 liter capacity were charged 200 g of 2,6-NDCA dimethyl, 185 g of glacial acetic acid, 185 g of benzoic acid, 30 g of water and 6.0 g of concentrated sulfuric acid and then temperature was raised at a heating rate of 5° C./min with stirring. After the temperature reached to 170° C., the reaction was continued at this temperature for 8 hours. Thereafter, the reaction product was cooled down to 60° C. and filtered by suction to remove the solvent. The thus obtained 2,6-NDCA was treated and confirmed by the same method as in Example 1 to have a purity of 99% and a whiteness degree of 93.7.

EXAMPLE 10

Into an autoclave of 1 liter capacity were charged 200 g of 2,6-NDCA dimethyl, 400 g of glacial acetic acid and 10 g of concentrated sulfuric acid and then temperature was raised at a heating rate of 5° C./min with stirring. After the temperature reached to 170° C., the reaction was continued at this temperature for 4 hours, during which high-pressure vapor (mixed gas of acetic acid and methyl acetate) was discharged out from the reaction system through a leak valve at every 15 minutes interval for the first one hour and at every 30 minutes interval for the remaining three hours. Thereafter, the reaction product was cooled and filtered by suction to remove the solvent. The thus obtained 2,6-NDCA was treated and confirmed by the same method as in Example 1 to have a purity of 100% and a whiteness degree of 93.5.

COMPARATIVE EXAMPLE 4

The same procedure as in Example 1 was repeated except that methacrylic acid was used instead of glacial acetic acid as a solvent. In this case, the gelation of the solvent was caused in the course of temperature rising, and consequently the ester exchange reaction did not proceed.

EXAMPLES 11-13

The same procedure as in Example 1 was repeated except that 12.0 g of concentrated hydrochloric acid (36%), 6.0 g of stannous chloride or 6.0 g of zinc chloride was added instead of 6.0 g of concentrated sulfuric acid. The measured results are shown in Table 2.

COMPARATIVE EXAMPLE 5

The same procedure as in Example 1 was repeated except that 6.0 g of concentrated sulfuric acid was not added. The results are also shown in Table 2.

TABLE 2

|  | Catalyst | Purity of 2,6-NDCA (%) | Whiteness degree of 2,6-NDCA |
|---|---|---|---|
| Comparative Example 5 | none | 0 | — |
| Example 11 | hydrochloric acid | 99 | 93.0 |
| Example 12 | stannous chloride | 45 | 91.6 |

TABLE 2-continued

| | Catalyst | Purity of 2,6-NDCA (%) | Whiteness degree of 2,6-NDCA |
|---|---|---|---|
| Example 13 | zinc chloride | 37 | 92.0 |

EXAMPLES 14–20, COMPARATIVE EXAMPLE 6

The same procedure as in Example 1 was repeated except that the reaction temperature was 50° C. (Comparative Example 6), 80° C., 110° C., 130° C., 140° C., 150° C., 160° C., or 200° C., (Examples 14–20). The results are shown in Table 3.

TABLE 3

| | Reaction temperature (°C.) | Purity of 2,6-NDCA (%) |
|---|---|---|
| Comparative Example 6 | 50 | 0 |
| Example 14 | 80 | 5 |
| Example 15 | 110 | 24 |
| Example 16 | 130 | 60 |
| Example 17 | 140 | 94 |
| Example 18 | 150 | 96 |
| Example 19 | 160 | 97 |
| Example 20 | 200 | 100 |

EXAMPLES 21–26

The same procedure as in Example 1 was repeated except that the amount of concentrated sulfuric acid added was 1 g, 2 g, 3 g, 4 g, 10 g or 15 g, and thereafter the contents (wt %) of 2,6-NDCA, 2,6-NDCA monomethyl and 2,6-NDCA dimethyl in the reaction product were measured by HPLC analysis. The results are shown in Table 4.

TABLE 4

| | Concentrated sulfuric acid (g) | 2,6-NDCA | 2,6-NDCA monomethyl | 2,6-NDCA dimethyl |
|---|---|---|---|---|
| | | Content (wt %) | | |
| Example 21 | 1 | 89.4 | 10.5 | 0.1 |
| Example 22 | 2 | 97.0 | 3.0 | 0 |
| Example 23 | 3 | 97.9 | 2.1 | 0 |
| Example 24 | 4 | 98.2 | 1.8 | 0 |
| Example 25 | 10 | 98.7 | 1.3 | 0 |
| Example 26 | 15 | 99.0 | 1.0 | 0 |

EXAMPLES 27–33, COMPARATIVE EXAMPLE 7, 8

Into the same reaction vessel as in Example 1 were charged 200 g of 2,6-NDCA dimethyl, 6.0 g of concentrated sulfuric acid and 400 g of an aqueous solution of acetic acid having a weight concentration of 100% (glacial acetic acid), 97.5%, 95%, 90%, 80%, 60%, 50% (Examples 27–33), 40% or 0% (water) (Comparative Examples 7, 8), which were reacted at 160° C. for 8 hours. The reaction product was subjected to HPLC analysis in the same manner as in Example 1. The results are shown in Table 5.

TABLE 5

| | Concentration of acetic acid (g) | 2,6-NDCA | 2,6-NDCA monomethyl | 2,6-NDCA dimethyl |
|---|---|---|---|---|
| | | Content (wt %) | | |
| Example 27 | 100 | 35.2 | 53.6 | 11.2 |
| Example 28 | 97.5 | 56.0 | 32.1 | 11.9 |
| Example 29 | 95 | 93.2 | 6.8 | 0 |
| Example 30 | 90 | 97.6 | 2.4 | 0 |
| Example 31 | 80 | 94.3 | 5.7 | 0 |
| Example 32 | 60 | 45.2 | 42.6 | 12.2 |
| Example 33 | 50 | 23.2 | 11.1 | 65.7 |
| Comparative Example 7 | 40 | 0.5 | 1.0 | 98.5 |
| Comparative Example 8 | 0 | 0 | 0 | 100 |

EXAMPLES 34, 35

The same procedure as in Example 1 was repeated except that 2,7-NDCA dimethyl or 1,5-NDCA dimethyl was used instead of 2,6-NDCA dimethyl. In any case, the corresponding NDCA was substantially quantitatively obtained. The results are shown in Table 6.

TABLE 6

| | Starting material | Purity of corresponding NDCA | Whiteness degree |
|---|---|---|---|
| Example 34 | 2,7-NDCA dimethyl | 99.2 | 95.0 |
| Example 35 | 1,5-NDCA dimethyl | 99.7 | 94.3 |

COMPARATIVE EXAMPLE 9

Into a reaction vessel were charged 100 g of 2,6-NDCA dimethyl, 60 g of potassium hydroxide and 120 g of water, which were reacted at 100° C. for 10 hours with stirring. The reaction solution changed to a high viscosity slurry. To the resulting slurry of 2,6-NDCA dipotassium salt was added 600 g of water to completely dissolve the slurry. The product thus obtained was subjected to filtration to separate unreacted solid 2,6-NDCA dimethyl. Then, the filtrate was adjusted to pH=3 by addition of hydrochloric acid. At the time of pH adjustment, white solid of 2,6-NDCA precipitated in form of a slurry. The viscosity of this slurry was measured to be 6500 centipoises, so that the solid-liquid separation was impossible owing to the high viscosity. For this end, the viscosity of the slurry was decreased to 1000 centipoises by further adding 600 g of water, whereby the solid-liquid separation was made by filtration under vacuum. Nextly, the procedures of washing and the solid-liquid separation were required three times with 1000 g in total of water to remove potassium chloride produced in the neutralization. Thereafter, 2,6-NDCA containing water after the washing was dehydrated by means of a centrifugal separating machine. The water content after the dehydration was 67% by weight. This product was dried to obtain 2,6-NDCA. The yield was 97%.

The analysis of metal ion content was carried out in the same manner as in Example 1, and showed that 2,6-NDCA contained 5200 ppm of potassium ion.

COMPARATIVE EXAMPLE 10

Into a reaction vessel were charged 60 g of 2,6-NDCA dimethyl, 26 g of sodium hydroxide and 100 g of water, which were reacted at 100° C. with stirring. With the lapse of time, the viscosity of the reaction solution increased and was completely solidified after 6 hours. As a result, the stirring was impossible, so that the reaction was stopped. In this case, the yield of 2,6-NDCA was 60%.

As mentioned above, according to the invention, the particular carboxylic acid acts as a starting material for ester exchange reaction and a solvent in the presence of an esterification catalyst, whereby a high purity naphthalene dicarboxylic acid can easily be obtained from a dialkylester of naphthalene dicarboxylic acid.

What is claimed is:

1. A method of producing naphthalene dicarboxylic acids, which comprises reacting a dialkylester of naphthalene dicarboxylic acid within a temperature range of 70°–350° C. in a solvent including at least one monocarboxylic acid represented by the following formula: R—COOH wherein R has a total carbon number of not more than 9 and is a hydrogen atom, an alkyl group, a cycloalkyl group, a phenyl group, a moiety selected from the group consisting of an alkyl, cycloalkyl, phenyl, alkylene, cycloalkylene and phenylene substituted by a carbonyl or an ether group, or alkyl, cycloalkyl or phenyl substituted by a different alkyl, cycloalkyl or phenyl, and a part or whole of hydrogen atoms in R may be substituted with halogen atom, provided that the total carbon number of R does not include a carbon number of carbonyl groups, in the presence of at least one esterification catalyst selected from the group consisting of strong acids, metal oxides, and metal salts and then subjecting the resulting reaction to a solid-liquid separation to obtain a high purify naphthalene dicarboxylic acid.

2. The method according to claim 1, wherein said solvent contains not more than 50% by weight of water.

3. The method according to claim 2, wherein said solvent contains not more than 20% by weight of water.

4. The method according to claim 1, wherein said reaction is carried out while removing out a resulting alkylester of monocarboxylic acid from the reaction system.

5. The method according to claim 1, wherein said dialkylester of naphthalene dicarboxylic acid is selected from the group consisting of dimethyl 1,5-naphthalene dicarboxylate, dimethyl 2,6-naphthalene dicarboxylate and dimethyl 2,7-naphthalene dicarboxylate.

6. The method according to claim 1, wherein said monocarboxylic acid is at least one acid selected from the group consisting of formic acid, acetic acid, propionic acid and benzoic acid.

7. The method according to claim 6, wherein said monocarboxylic acid is acetic acid.

8. The method according to claim 1, wherein said strong acid is at least one substance selected from the group consisting of sulfuric acid, nitric acid, hydrochloric acid, fluoroacetic acid, boron trifluoride and strong acid-type ion exchange resin.

9. The method according to claim 8, wherein said strong acid is sulfuric acid.

10. The method according to claim 1, wherein a metal of said metal oxide and said metal salt is selected from the group consisting of tin, zinc, lead, copper, manganese, cobalt, iron, nickel, antimony, aluminum, bismuth, selenium, tellurium, cadmium and mercury.

11. The method according to claim 1, wherein said temperature is 120°–200° C.

* * * * *